United States Patent [19]

Anderson et al.

[11] Patent Number: 5,187,987

[45] Date of Patent: Feb. 23, 1993

[54] BENDING BEAM CREEP TEST DEVICE WITH PISTON HAVING A GAS BEARING

[75] Inventors: David A. Anderson; John G. Witzel; Don Christensen; Hussain Bahia, all of State College, Pa.

[73] Assignee: The Pennsylvania Research Corporation, University Park, Pa.

[21] Appl. No.: 794,539

[22] Filed: Nov. 19, 1991

[51] Int. Cl.$^5$ ............................................... G01N 3/20
[52] U.S. Cl. ..................................... 73/852; 73/865.6
[58] Field of Search .......................... 73/849, 851–854, 73/865.6, 816, 798

[56] References Cited

U.S. PATENT DOCUMENTS

| | | | |
|---|---|---|---|
| 2,404,584 | 7/1946 | Liska et al. | 73/15.6 |
| 2,506,048 | 5/1950 | Van Den Akker | 73/100 |
| 2,670,624 | 3/1954 | Faris, Jr. et al. | 73/15.6 |
| 3,323,356 | 6/1967 | Arias | 73/852 |
| 3,324,714 | 6/1967 | Simon et al. | 73/853 |
| 3,640,127 | 2/1972 | Meissner | 73/95.5 |
| 3,831,438 | 8/1974 | Schmidt | 73/100 |
| 3,881,346 | 5/1975 | Scheucher | 73/95.5 |
| 4,033,181 | 7/1977 | Oeser | 73/88 A |
| 4,036,048 | 7/1977 | Webster | 73/81 |
| 4,096,741 | 6/1978 | Sternstein | 73/90 |
| 4,179,004 | 12/1979 | Ebbinge | 177/211 |
| 4,213,349 | 7/1980 | Miura | 73/852 |
| 4,266,424 | 5/1981 | Muenstedt | 73/15.6 |
| 4,478,086 | 10/1984 | Gram | 73/781 |
| 4,478,093 | 10/1984 | Valadier | 73/862.65 |
| 4,535,636 | 8/1985 | Blacksburn et al. | 73/831 |
| 4,589,288 | 5/1986 | Porter et al. | 73/849 |
| 4,679,441 | 7/1987 | Johnson et al. | 73/798 |
| 4,721,000 | 1/1988 | Scanlon | 73/833 |
| 4,730,498 | 3/1988 | Blanch | 73/852 |
| 4,763,529 | 8/1988 | Leonard et al. | 73/852 |
| 4,942,768 | 7/1990 | McRae | 73/795 |
| 4,982,609 | 1/1991 | Talley III | 73/849 |

*Primary Examiner*—Tom Noland
*Assistant Examiner*—Howard Wisnia
*Attorney, Agent, or Firm*—Thomas J. Monahan

[57] ABSTRACT

Apparatus is disclosed for measuring creep stiffness of a specimen, for example, asphalt cement, or other viscoelastic material, having a flexural modulus greater than approximately 1,000 psi. The specimen and the lower part of a loading mechanism are submerged in a constant temperature coolant thereby providing buoyant support to the specimen, preventing it from deflecting under its own weight, as well as providing means for controlling the test temperature. The coolant temperature is maintained to within approximately +/−0.1° C. of a desired temperature. The specimen, having known dimensions, is supported within the coolant on two spaced apart support members. A loading head actuated by an air bearing/pneumatic piston mechanism engages the specimen midway between the two support members. The deflection of the specimen is measured with an LVDT and the load imparted to the specimen by a load cell provided under at least one of the specimen support members. In order to prevent the buildup of frost on the apparatus, those components which extend from the air into the coolant are composed of low conductive material such as polymethylmethacrylate.

16 Claims, 3 Drawing Sheets

BENDING BEAM CREEP TEST DEVICE WITH PISTON HAVING A GAS BEARING

BACKGROUND OF THE INVENTION

1. Field of the Invention

The present invention relates generally to apparatus for rapidly and accurately measuring the flexural creep compliance, or creep stiffness, of asphalt cement, polymers, and other viscoelastic materials at temperatures at which they exhibit relatively high stiffness, generally greater than 1,000 psi.

2. Description of the Prior Art

The mechanical properties of some viscoelastic materials, that is, materials having some elasticity and slow flow or creep, cannot be determined by customary methods of shear rheometry. Their peculiar properties rather involve factors requiring a very considerable time element, as opposed to the rapid type of testing using shear rheometers. Also, there is a temperature factor which enters in the case of certain materials. One illustrative instance is the comparative measurement of asphalts as applicable to a determination of their characteristics for service life in pavements and the like. For instance, asphalt cement in pavement usage is subjected to stresses more particularly brought about by thermal expansion and contraction as caused by ambient temperature changes, freezing and thawing and the like. Hot-mix asphalt pavements are particularly characterized by their ability to undergo deformation, for example, to bend without breaking, in transmitting traffic loads to the foundation and natural sub-grade. In one sense, therefore, hot-mix asphalt pavements must be characterized by their response to stresses to include the effect of certain long-time factors affecting deformability.

Isolated properties such as penetration, softening point, and the like, as commonly determined for asphalt cements, are not sufficiently informative as to the overall behavior which may be expected of a given material in actual service life. Such fundamental properties as viscosity and elasticity enter, but extensive investigation has shown that these fundamental variables may change counter to each other with changes in temperature, and other environmental conditions, such that these individual characteristics are by themselves, of limited value in judging relative behavior of different materials.

Load-deformation response as a function of loading time and temperature, however, embodies the essential factors to such an extent that measurement of deformability becomes more convenient and practical as a basis of comparison. The present invention accordingly provides means by which deformability, at low stress levels, of asphalt, and materials generally which exhibit slow flow characteristics, may be relatively evaluated in a practical manner. One of the most important criteria of usefulness is the amount of cold flow under stress, commonly called creep. In the common forms of creep testing, the specimen is subjected to a torsion or shear load over a prolonged period of time. At various times during the period of loading, the deflection of the material is measured and subsequently plotted against time to serve as a measure of the fundamental engineering response of the material.

Determination of the creep compliance of asphalt cement at low temperatures is extremely important, since many pavement failures are caused by excessive stiffness of the asphalt binder at low temperatures. Previously, there was no simple and accurate means of determining the stiffness of asphalt cement at low temperatures. It was with knowledge of the existing situation that the present invention was conceived and is now reduced to practice.

SUMMARY OF THE INVENTION

In recognition of the foregoing, apparatus is disclosed for measuring creep stiffness of a specimen, for example, asphalt cement, or other viscoelastic material, having a flexural modulus in the range between approximately 1,000 and 500,000 psi. The specimen and the lower part of a loading mechanism are submerged in a constant temperature coolant thereby providing buoyant support to the specimen, preventing it from deflecting under its own weight, as well as providing means for controlling the test temperature. Within the coolant, the specimen, having known dimensions, is supported at its ends on two spaced apart support members. A loading head actuated by an air bearing/pneumatic piston mechanism engages the specimen midway between the two support members. The deflection of the specimen is measured with an LVDT and the load imparted to the specimen by a load cell provided under at least one of the specimen support members. In order to prevent the buildup of frost on the apparatus, those components which extend from the air into the coolant are composed of low conductive material such as polymethylmethacrylate.

The bending beam test of the invention represents a significant improvement in the applied technology of asphalt testing and specifications, and once in wide use, should result in improvements in pavement performance in regions where low temperature cracking of pavements is a problem.

In order to measure the rheological properties of asphalt cement, various test modes and geometries may be used. The general problem is to apply a known stress or strain to a specimen, measure the resulting response, and calculate the desired rheological parameter, such as dynamic modulus, creep compliance, or relaxation modulus. The measurement of such mechanical properties at low temperatures is particularly difficult, because asphalt cement and similar materials become very stiff and brittle under these conditions. Many tests suitable for use at higher temperatures will not provide accurate results at low temperatures. For this reason, the inventors developed the bending beam test device, which is described in greater detail below.

As noted above, devices are commercially available which can be used to measure the mechanical properties of materials in bending. However, they tend to be expensive, complex, and require special knowledge and training for their proper operation.

A primary advantage of the bending beam test device of the invention compared to existing practice is that it provides an extremely accurate means of measuring the flexural creep compliance or stiffness of asphalt cement and polymers at low temperatures, and is simple to perform, rapid in execution, and relatively inexpensive.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
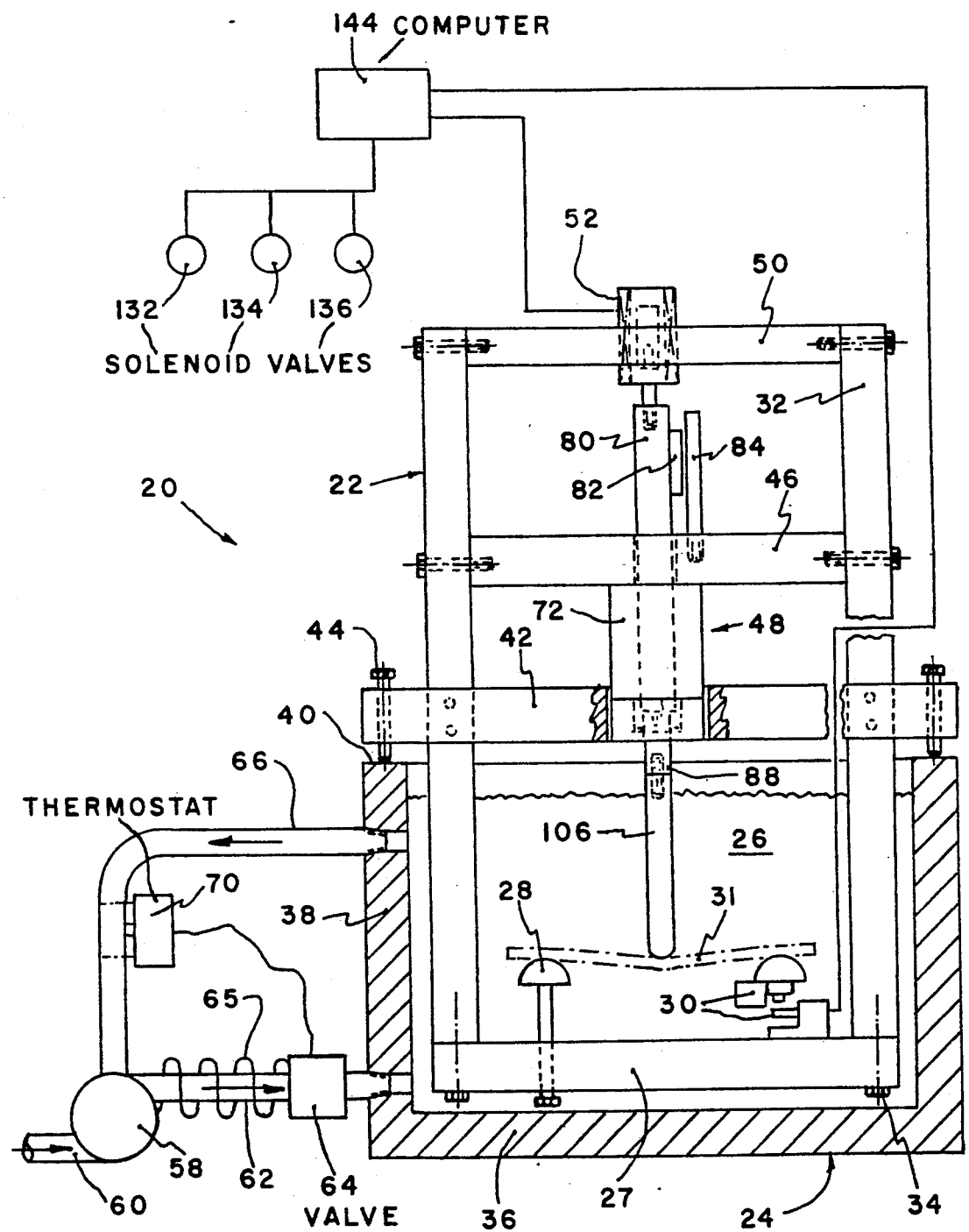
FIG. 1 is a diagrammatic side elevation view of a loading bending beam creep test device embodying the present invention.

Turn now to the drawings and, initially, to FIG. 1, which diagrammatically illustrates a bending beam creep test device 20 embodying the invention. Its purpose is to measure the flexural creep compliance and/or creep stiffness of asphalt cement and similar materials at low temperatures. Although the device was originally developed for use in testing asphalt cement, it can be used without modification for testing polymers, composites, and similar materials. The only constraint is that the creep stiffness of the specimen to be tested should be greater than about 1000 psi. A primary advantage of the bending beam creep test device 20 compared to known devices is that it can provide very accurate data on the flexural creep compliance, or stiffness, of viscoelastic materials at low temperature.

The device itself is relatively inexpensive and requires no special knowledge or skills for its operation. It is therefore a very attractive alternative to the more expensive and complicated rheological test devices presently in use.

There are several key problems which are typically encountered in the measurement of viscoelastic properties at low temperature and which have been solved in the design and construction of the present invention. Viscoelastic measurements are most commonly made under shear loading. When a very stiff material is tested in shear, the deflections are, therefore, very small and difficult to measure accurately. However, by using the bending beam test geometry of the invention, much larger deflections are possible than would otherwise be the case, thus greatly improving the accuracy of the test. Furthermore, in recognition of the fact that a beam loaded in flexure normally deflects somewhat under its own weight, the test device 20 has been developed so that the specimen is loaded in a bath composed of a liquid coolant. Asphalt cement, and most polymers, have a specific gravity very close to that of water and by performing the test in a fluid bath, the effective weight of the specimen becomes negligible, eliminating this source of error.

With particular attention to FIG. 1, a frame assembly 22 is illustrated inserted within a commercially available fluid bath 24 containing a liquid coolant 26. The coolant 26 may be of a variety of compositions suitable for testing a specific material which is the subject of the investigation. In addition, it should be capable of quickly achieving, then maintaining, the testing temperature without freezing or becoming unduly viscous.

The frame assembly 22 includes a generally level base 27 and a pair specimen support members 28 upstanding from the base at spaced apart locations. A suitable transducer in the form of a load cell 30 may be associated with one of the support members 28 for measuring the magnitude of a load imparted to a specimen 31 supported on the support members 28. A plurality of upright members 32 are suitably fixed to the base 27 as by fasteners 34.

The basin 24 includes a bottom 36 and upstanding side walls 38 which terminate at an upper rim 40 which lies substantially in a horizontal plane. A frame support member 42 is suitably fixed to the upright members 32 and overlies the upper rim 40 and a plurality of leveling screws 44 mounted around the periphery of the frame support member 42 engage the upper rim 40 and are adjustable to alter the relative positioning of the frame support member 42, preferably to maintain it in a substantially horizontal attitude. A first platform 46, spaced above the frame support member 42 and generally parallel thereto is fixed to the upright members 32 and serves to mount an actuator 48 which will be described below in detail.

Figure 2:
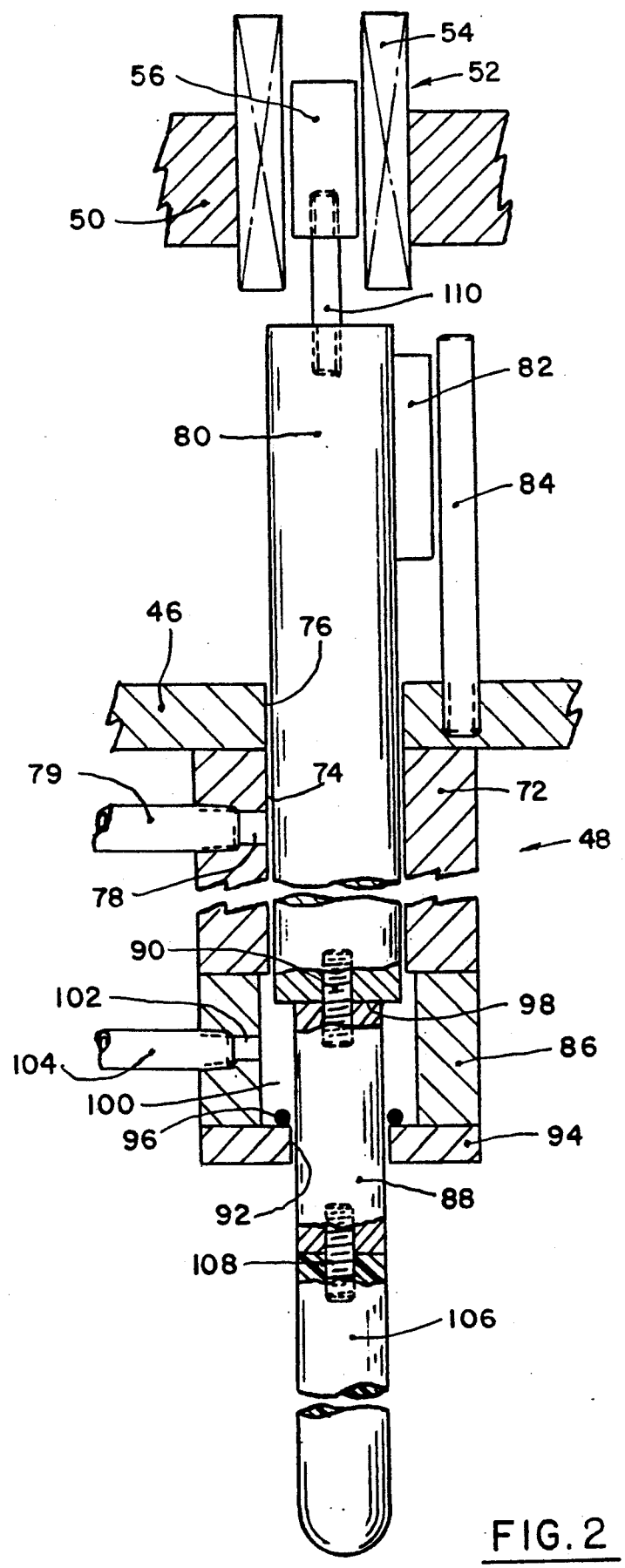
FIG. 2 is a detail side elevation view of certain components illustrated in FIG. 1.

A second platform 50, also lying in a plane generally parallel to that of the frame support member 42 is also mounted to the upright members 32, being positioned above the first platform 46. The second platform serves primarily to mount an LVDT (Linear Variable Differential Transformer) or transducer 52. In actual fact, a coil 54 of the LVDT 52 is fixed to the platform 50 while a core 56 thereof is freely movable in a vertical direction (see FIG. 2).

It was earlier mentioned that the specimen 31 is immersed in the liquid coolant 26 within the basin 38. It is important for purposes of the invention to maintain the temperature of the coolant at a substantially uniform temperature. Indeed for best results, the coolant 26 should be maintained within approximately + or −0.1° C. of a desired temperature for any particular test. To this end, liquid coolant is delivered to the basin 24 by means of a suitable pump 58 drawing the coolant from a supply line 60, then directing it via an inlet line 62, through a valve 64, then through the side wall 38 into the interior of the basin 34. A coil 65 for refrigerating the coolant surrounds the inlet line 62 and maintains the coolant at a predetermined temperature. Thus, coolant is applied to the bottom of the basin 24 and, by means of an outlet line 66, coolant at a somewhat warmer temperature is drawn from the upper regions of the basin.

In order to maintain the temperature of the coolant 26 within the basin 24 at a substantially uniform temperature, the valve 64 in the inlet line 62 is controlled by a thermostat 70 which is responsive the temperature in the outlet line 66. Thus, as the temperature of the coolant in the line 66 increases, the valve 64 opens to admit a greater flow of refrigerated coolant into the basin 24. However, so long as the temperature differential between the coolant in the inlet line 62 and the outlet line 66 remains at a minimum, then the valve 64 is either closed or only opened to a moderate extent. With a greater temperature differential, the valve 64 is either initially opened or opens to a greater extent to allow a greater flow of coolant into the basin.

It was earlier stated that the actuator 48 is mounted on the first platform 46. The construction of the actuator 48 is illustrated in greater detail in FIG. 2. As seen in that figure, the actuator includes an outer cylinder 72 which is suitably fixed to the first platform 46 and has an inner diameter 74 which is generally coextensive with an aperture 76 which extends through the platform 46.

An inlet 78 which is in communication with the interior of the cylinder 72 admits pressurized fluid into the cylinder surrounding a piston 80 which is received within the cylinder 72 for movement relative thereto in a longitudinal direction. In a typical construction, the piston 80 is of a diameter such that there is a clearance of approximately 0.0001 inches of clearance with the outer cylinder 72. Riding on a cushion of air as provided through the inlet 78, the piston 80 moves in a substantially friction free manner. For optimal results of the actuator, it is important the piston 80 be held against rotation relative the outer cylinder 72. At the same time, any mechanical expedient to achieve this end would create friction and necessarily result in a diminution of the effectiveness of the actuator. In order to achieve this result, then, a magnet 82 is suitably attached to the outer peripheral surface of the piston 80 at a location above the platform 46 and an upright ferrous post 84 is mounted at its base to the platform 46 and extends generally parallel to a longitudinal axis of the piston 80 and only slightly spaced from the magnet 82. Thus, as the piston 80 moves longitudinally relative to the cylinder 72, the magnet 82 is constantly attracted to the ferrous post 84 thereby maintaining the azimuthal position of the piston 80 with respect to the cylinder 72. In this manner, the piston 80 is frictionlessly prevented from rotating even as it moves longitudinally in a substantially frictionless manner.

A lower cylinder 86 has an inner diameter slightly larger than that of the cylinder 72. Additionally, a loading shaft 88 axially aligned with the piston 80 and fixed thereto as by a connecting stud 90 has a diameter substantially less than that of the piston. The loading shaft extends away from the piston through the cylinder 86, then through an aperture 92 in a cylinder seal 94 sealingly affixed to the free end of the cylinder 86. An 0-ring 96 which has an outer diameter substantially similar to that of the piston 80 surrounds the loading shaft 88 adjacent the aperture 92 and serves to cushion the impact when a lowermost end 98 of the piston advances toward the cylinder seal 94.

Pressurized fluid can also be introduced into a chamber 100 defined, respectively, by the piston 80, the cylinder 86, the loading shaft 88, and the cylinder seal 94. This is achieved from a suitable source via an inlet 102 and associated fitting 104. It is in this manner that load applied to the test specimen 31 is controlled. That is, as the applied air pressure exerts an upward force on the lowermost end 98 of the piston 80, it reduces the load generated by the gravitational pull of the piston applied to the specimen. Indeed, the pressure within the chamber 100 can actually increased to a point at which the piston 80 and its components are weightless and float supported only by a cushion of air. The actuator 48 is extremely sensitive to pressure changes and, therefore, can apply very accurate loads to the specimen 31.

During the initial effort on the development of the test device of the invention, it was found that the frame assembly 22, loading shaft 88, and associated bearings rapidly became covered with frost or ice when testing at very low temperatures. In order to eliminate this problem, all parts of the test device which extend from the air into the coolant are now composed of a substantially non-conducting material of relatively high stiffness. One suitable material for this purpose has been found to be polymethylmethacrylate or other suitable material of low thermal conductivity. Such an expedient has totally the eliminated the build-up of frost or ice on the device even when testing at the lowest temperatures previously indicated. Accordingly, it is preferred that the upright members 32 be fabricated from such a material. Additionally, a nose member 106 of a such a material with the same external dimensions as the loading shaft 88 is affixed to the loading shaft as by a suitable stud 108. The lowermost end of the nose member 106 is rounded so as to minimize unintended deformation of the specimen 31.

In the past, a major difficultly in performing creep such as performed by the test device of the invention has been providing for a properly zeroed configuration prior to application of the load. That is, immediately before starting a test, the deflection sensor must be in contact with a specimen, but there must be essentially no load on the specimen. For the bending beam test device of the invention, the deflection is measured by the LVDT 52 whose core 56 is connected to the piston 80 by means of a stud 110. Thus, while the loading shaft 88, through its nose member 106, must be in contact with the specimen 31, it must be resting with little or no weight on its surface. The actuator 48, just described, has successfully solved this problem since the pressure to the piston via inlet 102 can be gradually adjusted to balance, or zero, the weight of the piston 80 and its associated components. During a test, one or more relay valves can be used to apply or change the load in a nearly instantaneous fashion. For reproducible loads, high precision regulators are used in conjunction with a pneumatic loading system 112.

Figure 3:
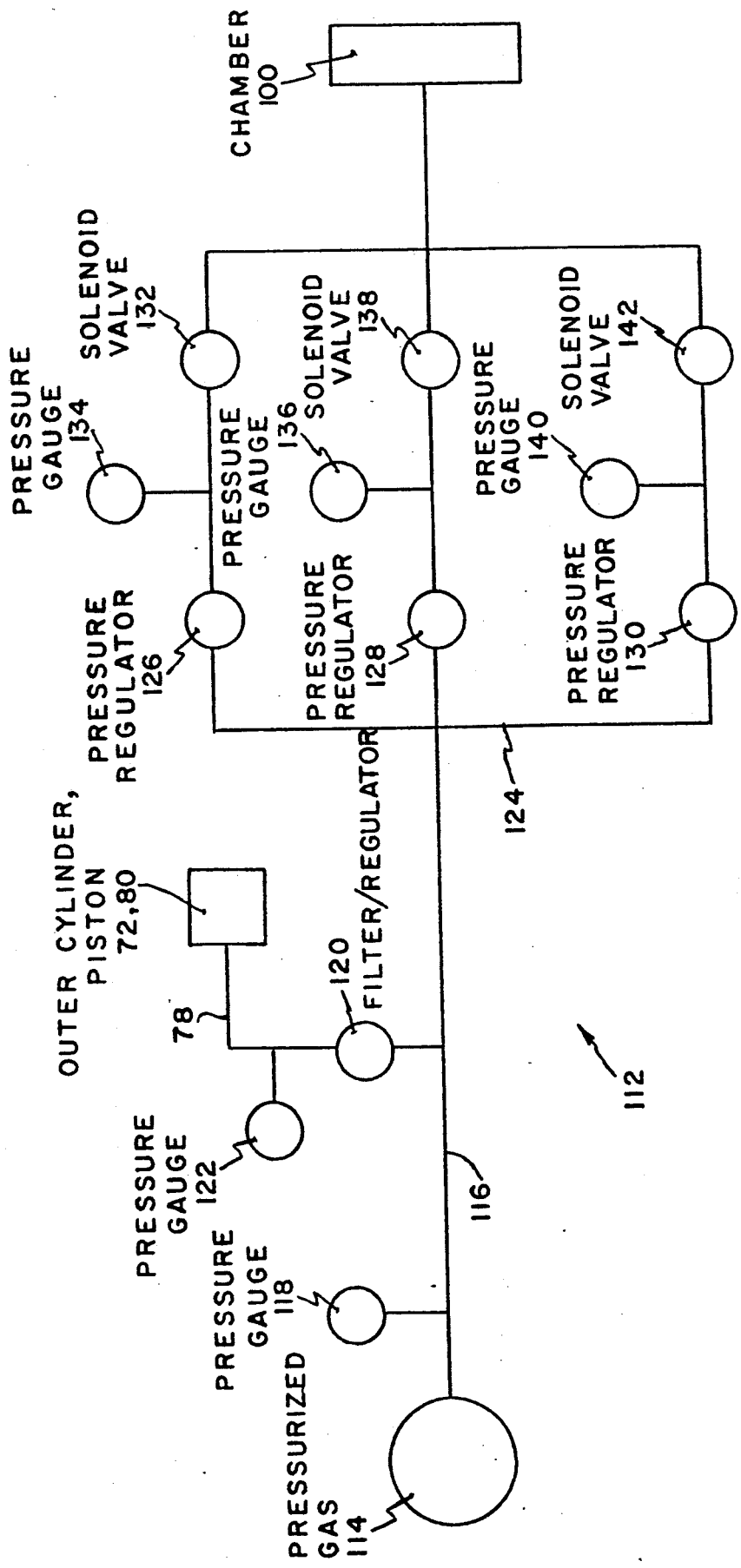
FIG. 3 is a schematic diagram of the pneumatic loading system used for operating the test device of the invention.

Turn now to FIG. 3 for an explanation of the pneumatic loading system 112 which is used in conjunction with the test device 20. In FIG. 3, a source of pressurized gas 114 which may be air or nitrogen, for example, is suitably regulated for a pressure adequate for operating the actuator 48. Following a fluidic path as represented by a pressurized gas line 116, a pressure gauge 118 is encountered which indicates the raw inlet pressure prior to any internal regulation. Thereafter, a line which leads to inlet 78 for applying pressurized gas to the outer cylinder 72 for supporting the piston 80 includes a combination filter and regulator 120. The filter is utilized because of the very close tolerances between the inner diameter 74 and the outer diameter of the piston 80. The filter/regulator 120 also reduces the line pressure to the appropriate value for application to the inlet 78. A gauge 122 monitors this latter pressure.

The pressurized gas line 116 is also routed to a low pressure regulator manifold 124. This manifold has one or more high precision, low pressure regulators 126, 128 and 130 attached to it. By means of a solenoid valve 132, the regulator 126 operates to deliver to the chamber 100, via inlet 102, a "no load" pressure as-indicated by a gauge 134. By reason of the "no load" pressure, the lowermost end of the nose member 106 engages the test specimen 31, but the piston 80 and its associated components including the loading shaft 88 and nose member 106 are fully balanced so that, in fact, no load is applied to the test specimen. The pressure regulator 128 admits a "load 1" as indicated by a gauge 136 to the chamber 100 upon operation of a solenoid valve 138. The "load 1" pressure would be of a magnitude less than "no load" admitted by the solenoid valve 132. This would result in a load of a predetermined magnitude being applied to the test specimen. Finally, the regulator 130 is operable to admit a "load 2" pressure, as indicated by a gauge 140 upon operation of a solenoid valve 142. The pressure admitted by the regulator 130 may be still less than that admitted by the regulator 128, resulting in a still greater load being applied to the test specimen.

As indicated in FIG. 1, the entire operation of the test device 20 is preferably controlled and coordinated by a computer 144.

In the operation of the test device 20, a test specimen 31 which by way of example may be five inches long by one half inch wide by one quarter inch thick is loaded in three point bending as depicted in FIG. 1. The load applied to the specimen is measured by the load cell 30 beneath one of the support members 28. The deflection imparted to the test specimen is measured by the LVDT 52 which is connected directly to the upper end of the structure including the loading shaft 88. The creep compliance or creep stiffness can be calculated from the load, the deflection, and the specimen dimensions by equations dictated by the theory of elasticity and application of a correspondence principle which provides a linear viscoelastic solution to the determination of the mechanical properties given the load deflection curve.

The test is carried out with the specimen 31, and the lower part of the frame assembly 22 and nose member 106 of loading shaft 88, submerged in the controlled temperature liquid coolant 26. This construction provides rapid and accurate control of the test temperature. Additionally, the coolant 26 provides flotation to the specimen 31, preventing it from deflecting excessively from its own weight.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. Apparatus for measuring creep stiffness of a specimen composed of viscoelastic material having a flexural modulus greater than approximately 1,000 psi comprising:
    a basin containing liquid coolant into which the specimen to be tested is immersed for maintaining the specimen at a predetermined temperature and for uniformly buoying the specimen;
    first and second support means for supporting the specimen at spaced apart finite locations within the liquid coolant;
    actuator means including:
    a loading head for imparting a bending load to the specimen intermediate said support means;
    a piston integral with said loading head;
    gas bearing means supporting said piston for substantially frictionless movement as said loading head is moved between an advanced position and a retracted position; and
    a source of pressurized gas for moving said piston between said advanced position and said retracted position;
    first transducer means for measuring the deflection load imparted to the specimen; and
    second transducer means for measuring the deflection sustained by the specimen as a result of the imparted load.

2. Apparatus as set forth in claim 1 wherein said liquid coolant means includes:
    means for delivering liquid coolant to said basin.

3. Apparatus as set forth in claim 1 including means for controlling the temperature of the liquid coolant in said basin.

4. Apparatus as set forth in claim 3 wherein said temperature controlling means includes means to control the temperature of the liquid coolant to a temperature within approximately $+/-0.1°$ C. of a desired temperature.

5. Apparatus for measuring creep stiffness of a specimen composed of viscoelastic material having a flexural modulus greater than approximately 1,000 psi comprising:
    a basin for containing a liquid coolant approximately $+/-0.1°$ C. of a desired temperature including a bottom and upstanding side walls terminating at an upper rim lying in a horizontal plane;
    a frame assembly adapted to be mounted on said basin including:
    a base;
    a pair of specimen support members upstanding from said base at spaced apart locations;
    first transducer means associated with at least one of said specimen support members for measuring the magnitude of the load imparted to the specimen;
    a plurality of upright members mounted on said base;
    acutator means including:
    a loading head for imparting a load to the specimen intermediate said specimen support members;
    a piston integral with said loading head;
    gas bearing means supporting said piston for substantially frictionless movement as said loading head is moved between an advanced position and a retracted position; and
    a source of pressurized gas for moving said piston between said advanced position and said retracted position;
    first platform means fixed to said upright members for mounting said actuator means;
    second transducer means for measuring the magnitude of a deflection sustained by the specimen and as a result of the imparted load;
    second platform means fixed to said upright members for mounting said transducer means;
    a frame support member fixed to said upright members overlying said upper rim of said basin; and
    leveling adjustment means on said frame support member engageable with said upper rim.

6. Apparatus for measuring creep stiffness as set forth in claim 5 comprising:
    a source of liquid coolant; and
    means for delivering liquid coolant from said source to said basin.

7. Apparatus for measuring creep stiffness as set forth in claim 6 including means for controlling the temperature of the liquid coolant in said basin.

8. Apparatus for measuring creep stiffness as set forth in claim 1
    wherein said second transducer means, said piston, and said loading head are all aligned along an upright axis.

9. Apparatus for measuring creep stiffness as set forth in claim 8 including non friction means for preventing rotation of said piston as said loading head is moved between said advanced and said retracted positions.

10. Apparatus for measuring creep stiffness as set forth in claim 9
    wherein said piston has a cylindrical outer surface; and
    wherein said non-friction means for preventing rotation includes:

an elongated magnet fixed to said outer surface of said piston substantially parallel to said upright axis; and an upright metallic post fixed to said first platform means generally parallel to said upright axis and spaced from said magnet to effect strong magnetic attraction between said magnet and said post while preventing physical engagement therebetween.

11. Apparatus for measuring creep stiffness as set forth in claim 5 wherein said upright members and said loading head are composed of insulating materials.

12. Apparatus for measuring creep stiffness as set forth in claim 5 wherein said upright members and said loading head are composed of polymethylmethacrylate.

13. Apparatus for measuring creep stiffness as set forth in claim 1 wherein said loading head is composed of insulating material.

14. Apparatus for measuring creep stiffness as set forth in claim 1 wherein said loading head is composed of polymethylmethacrylate.

15. Apparatus for measuring creep stiffness as set forth in claim 5
wherein said second transducer means, said piston, and said loading head are all aligned along an upright axis.

16. Apparatus for measuring creep stiffness as set forth in claim 15 including non friction means for preventing rotation of said piston as said loading head is moved between said advanced and said retracted positions.

* * * * *